United States Patent [19]

Peake et al.

[11] Patent Number: 5,502,054

[45] Date of Patent: Mar. 26, 1996

[54] 6-SUBSTITUTED-3,5-DIAMINO-1,2,4-TRIAZINES AS INSECTICIDES

[75] Inventors: Clinton J. Peake, Trenton; Thomas G. Cullen, Milltown, both of N.J.

[73] Assignee: FMC Corporation, Philadelphia, Pa.

[21] Appl. No.: 424,144

[22] Filed: Apr. 18, 1995

Related U.S. Application Data

[63] Continuation-in-part of Ser. No. 338,288, Nov. 10, 1994, abandoned, which is a continuation of Ser. No. 289,080, Aug. 11, 1994, abandoned.

[51] Int. Cl.$^6$ .................... C07D 253/075; A01N 43/707
[52] U.S. Cl. ............... 514/242; 544/182; 514/63
[58] Field of Search ............... 544/182; 514/242, 514/63

[56] References Cited

U.S. PATENT DOCUMENTS

| | | | |
|---|---|---|---|
| 2,976,288 | 3/1961 | Green et al. | 260/249.9 |
| 3,105,074 | 9/1963 | Mamalis | 260/249.9 |
| 3,637,688 | 1/1972 | Rees et al. | 260/249.9 |
| 3,660,394 | 5/1972 | Mamalis | 260/249.9 |
| 3,682,912 | 8/1972 | Mamalis et al. | 260/249.9 |
| 3,723,429 | 3/1973 | Mamalis et al. | 260/249.9 |
| 3,980,774 | 9/1976 | Hegarty et al. | 424/166 |
| 4,027,039 | 5/1977 | Hegarty et al. | 424/326 |
| 4,032,659 | 6/1977 | Hegarty et al. | 424/274 |
| 4,425,155 | 7/1982 | Dumas | 544/182 |
| 4,563,456 | 1/1986 | Kuhla et al. | 424/326 |

FOREIGN PATENT DOCUMENTS

| | | |
|---|---|---|
| 2003144 | 1/1970 | Germany . |
| 3901084 | 1/1989 | Germany . |
| 7025903 | 1/1968 | Japan . |
| 1053113 | 4/1963 | United Kingdom . |
| 1053307 | 4/1963 | United Kingdom . |
| 1297273 | 11/1972 | United Kingdom . |

OTHER PUBLICATIONS

Coates et al., "Comparative Q SAR of Antibacterial Dihydrofolate Reductase Inhibitors, QSAR in Design of Bioactive CMPDS", 84, Ed. by M. Kuchar, Prous, 71–85 (Apr. 6, 1992).
R. L. Blakely, "The Biochemistry of Folic Acid and Related Pteridines", John Wiley and Sons, p. 467 (1969).
Blaney, Jeffrey M., et al., Chemical Reviews (A.C.S.), vol. 84, No. 4 (1984), pp. 333–407.
Manteuffel-Cymborowska, Malgorzata, et al., J. Insect. Physiol., vol. 16, (1970), pp. 1419–1428.
Baker, B. R., J. Med. Chem., vol. 10 (1967), pp. 912–917.
Mamalis, "Amino-oxy-derivatives. Part III. Dihydrotriazines and Related Heterocycles" J. Chem. Soc. (1962) 3915–26.
Mamalis, "Aminooxy Derivatives. IV. Antimicrobial Activity of Some O-Ethers of 4,6-Diamino-1,2-dihydro-1-hydroxy-2-substituted 1,3,5-Triazines" J. Med. Chem. (1965) 8, 684–91.
Mamalis, "Amino-oxy-derivatives. Part V. Some O-Ethres of 2-Substituted 4,6-Diamino-1,2-dihydroxy-1,
3,5-triazines" J. Chem. Soc. (1965) 1829–43.
Knight, "The antimalarial activity of N-benzyl-oxydihydrotriazines" Ann. Trop. Med. and Paras. (1982) 76, No. 1 (1–7).
Mamalis, "Amino-oxy-derivatives Part II. Some Derivatives of N-Hydroxydiguanide" J. Chem. Soc. (1960) 229–238.
Sanemitsu et al, "5-Substituted Amino-3,6-Dichloro-1,2, 4-Triazines as New Potential Herbicides", Agric. Biol. Chem., 54 (12), 3367–69 (1990).
ACS CAS Online® Abstrcts: 1,2,4-Triazine-3,5-Diamines (Registry File Search Results-73 Non-consecutive pages) (1995).
Bhalla et al., Chemical Abstracts, vol. 68, entry 104123 (1968).
Rees et al., Chemical Abstracts, vol. 77, entry 122 123 (1972).
Rees et al., Chemical Abstracts, vol. 76 entry 113258 (1972).
Hegarty et al., Chemical Abstracts, vol. 85, entry 154151 (1976).
Hegarty et al., Chemical Abstracts, vol. 87 entry 112003 (1977).
Hegarty et al., Chemical Abstracts, vol. 87 entry 33694 (1977).
Roth et al., Chemical Abstracts, , vol. 95, entry 30402 (1981).

(List continued on next page.)

*Primary Examiner*—John M. Ford
*Attorney, Agent, or Firm*—Stanford M. Back; Robert M. Kennedy

[57] ABSTRACT

An insecticidal composition comprising, in admixture with an agriculturally acceptable carrier, an insecticidally effective amount of a 1,2,4-triazine compound of the formula

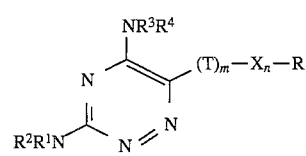

wherein
m is 0 to 12; n is 0 or 1; T is $CH_2$, $CH=CH$, or $C\equiv C$; X is $Si(CH_3)_2$, $C(CH_3)_2$, $CH(CH_3)$, or O; or R is methyl, vinyl, cyclopentyl, phenyl, naphthyl, or a substituted phenyl of the formula:

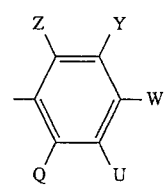

wherein
Q, U, W, Y, Z, and $R^1$, $R^2$, $R^3$, $R^4$ are as defined herein; and methods of using the same.

15 Claims, No Drawings

OTHER PUBLICATIONS

Baxter et al. Chemical Abstracts, vol. 94, entry 208914 (1981).

Baxter et al., Chemical Abstracts, vol. 98, entry 89397 (1982).

Allan et al., Chemical Abstracts, vol. 103, entry 142021 (1985).

Kuhla et al., Chemical Abstracts, vol. 104, entry 200211 (1986.

6-SUBSTITUTED-3,5-DIAMINO-1,2,4-TRIAZINES AS INSECTICIDES

RELATED APPLICATIONS

This application is a continuation-in-part of application Ser. No. 08/338,288, filed Nov. 10, 1994 in the names Peake et al., now abandoned which application is a continuation of application Ser. No. 08/289,080, filed Aug. 11, 1994 (now abandoned).

BACKGROUND OF THE INVENTION

This invention relates to substituted 1,2,4-triazine compounds and compositions containing the same (hereinafter "substituted triazines") which are useful for controlling insects in agricultural crops. More particularly, this invention relates to certain 6-substituted 3,5-diamino-1,2,4-triazine compounds and compositions, and their use as insecticides against a variety of insects, including larvae such as the tobacco budworm.

SUMMARY OF THE INVENTION

In accordance with the present invention it has been found that certain substituted triazines, as defined hereinbelow, and agriculturally acceptable salts thereof, when present in insecticidally effective amounts and with a suitable agricultural carrier, are useful as active ingredients in the insecticidal compositions and methods of this invention. These substituted triazines may be represented by the following generic structure:

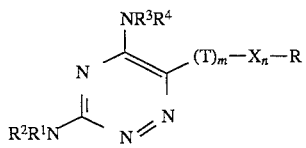

wherein m is 0 to 12; n is 0 or 1; T is $CH_2$, $CH=CH$, or $C\equiv C$; X is $Si(CH_3)_2$, $C(CH_3)_2$, $CH(CH_3)$, or O; and R is methyl, vinyl, cyclopentyl, phenyl, naphthyl, or a substituted phenyl of the formula:

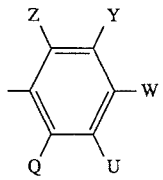

wherein

Q is hydrogen or chloro; U is hydrogen, chloro, trifluoromethyl, phenyl, or 4-fluorophenyl; W is hydrogen, ethyl, chloro, trifluoromethyl, or propylsulfonyl; Y is hydrogen, chloro, bromo or trifluoromethyl; and Z is hydrogen;

$R^1$, $R^2$, $R^3$, and $R^4$ are independently selected from the group consisting of hydrogen, $-CH_3$, $-C_2H_5$, or $-C(=O)R^5$, where $R^5$ is straight or branched chain lower alkyl of one to three carbon atoms, $-CH_2OCH_2CH_3$, $-CH_2OCH_2CH_2CH_3$, $-CH_2CH_2OCH_3$, or $-CH_2CH_2OCH_2CH_3$;

with the proviso that when T is alkylene or acetylene, m must be 1;

and agriculturally acceptable salts thereof.

Agriculturally acceptable salts of the 1,2,4-triazines include, but are not limited to, for example, the salts of hydrochloric acid, ethanesulfonic acid, gluconic acid, and pamoic acid.

Of the compounds of the present invention, the more preferred ones are those of formula (I) wherein R is methyl or phenyl; X is $Si(CH_3)_2$; m is 2 or 3; and n is 1. See, in particular, Compounds 8 and 14 of Table 1.

DETAILED DESCRIPTION OF THE INVENTION

Synthesis of The Compounds

The compounds employed in the insecticidal composition of this invention are generally known, or may readily be prepared by methods known to those skilled in the art. For example, Schemata 1 and 2, below, describe two general methods of synthesizing the 3,5-diamino-6-substituted-1,2,4-triazines of the present invention. In Schema 1 a substituted alcohol is oxidized in chromium trioxide and sulfuric acid to the corresponding acid (I). The acid chloride of (I) is then prepared by treating the acid with oxalyl chloride in the presence of a catalytic amount of N,N-dimethylformamide, producing (II). Heating the acid chloride (II) with copper(I) cyanide produces the corresponding alkanoyl cyanide (III). The reaction of (III) with aminoguanidine in the presence of nitric acid in dimethyl sulfoxide produces the corresponding N-[(substituted)(cyano)methylidene]-N'-diaminomethylidenehydrazine (IV). Closure of intermediate (IV) to the desired 3,5-diamino-6-substituted-1,2,4-triazine (V) is effected by treating (IV) with potassium hydroxide in ethanol. This method is detailed in Example 1, and parts of it are utilized in Examples 3 and 4.

An alternative synthesis route to the 3,5-diamino-6-substituted-1,2,4-triazines is shown in Schema 2. This method starts with the preparation of the Grignard reagent of a substituted methyl chloride (VI). The Grignard reagent is then added to ethyl acrylate, forming the corresponding ethyl substituted propionate (VII). Diethyl oxalate is then reacted with (VII) in the presence of sodium ethoxide, producing the corresponding 3-(substituted ethyl)-2-oxosuccinate (VIII). Heating (VIII) in the presence of tetrabutyl ammonium hydroxide produces the corresponding 4-substituted-2-oxopentanoic acid (IX). Reacting (IX) with aminoguanidine in the presence of hydrochloric acid then produces the corresponding N-[(3-substituted-propyl)(carboxy)methylidene]-N'-diaminomethylidenehydrazine (X). Closure of (X) may be effected by heating (X) with an aqueous solution of potassium carbonate, producing the corresponding 3-amino-5-hydroxy-6-(3-substituted-propyl)-1,2,4-triazine (XI). Treatment of (XI) with phosphorus pentasulfide in pyridine produces the corresponding 3-amino-5-mercapto-6-(3-substituted-propyl)-1,2,4-triazine (XII). Heating intermediate (XII) with ammonia in ethanol results in the production of the corresponding 3,5-diamino-6-(3-substituted-propyl)-1,2,4-triazine (V). This method of synthesizing the instant compounds is detailed in Example 2.

The synthesis of intermediates leading to different values of m and X is within the capability of one skilled in the art. Example 3 details the method of making the compound wherein X is $-CH(CH_3)-$ and m is 2. This synthesis starts with the reduction of 2-(4-chlorophenyl)propionic acid with lithium aluminum hydride, producing 2-(4-chlorophenyl)propanol. Oxidation of this alcohol with pyridinium chlorochromate in methylene chloride produces 2-(4-chlorophenyl)propionaldehyde. This aldehyde is then reacted with (carbethoxymethylene)triphenylphosphorane, yielding ethyl 4-(4-chlorophenyl)-2-pentenoate. Hydrogenation of this ester in the presence of platinum oxide produces ethyl 4-(4-chlorophenyl)pentanoate which is then hydrolyzed with sodium hydroxide to the corresponding pentanoic acid (II). The remaining steps of this synthesis are shown in Schema 1.

Synthesis of an intermediate in which m is 3 is detailed in Example 4. This route starts with the reaction of 3-butyn-1-ol with 2,4-dichloroiodobenzene in the presence of bis-(triphenylphosphine)palladium(II) chloride and copper(I) iodide in acetonitrile and triethylamine, producing 4-(2,4-dichlorophenyl)-3-butyn-1-ol. Hydrogenation of this acetyleneic alcohol over platinum oxide produces 4-(2,4-dichlorophenyl)-1-butanol which is then oxidized with chromium trioxide and sulfuric acid to the corresponding carboxylic acid. The remaining steps are the same as those detailed in Example 1.

Compounds of the present invention wherein T is CH=CH or C≡C, X is C(CH$_3$)$_2$ and m and n are 1 are prepared by methods known in the art. For example, in Schema 3 where T is CH=CH, 3-methyl-2-butenal is reacted with an appropriately substituted Grignard reagent in the presence of copper(I) bromide, yielding the corresponding 3-substituted-3-methylbutyraldehyde, for example, 3-(4-chlorophenyl)-3-methylbutyraldehyde. The aldehyde is subsequently treated with n-butyllithium and tributyltin hydride, affording the 3-substituted-3-methyl-1-tributylstannylbutanol. This intermediate is then halogenated with iodine in the presence of triphenylphosphine and imidazole, giving the corresponding 3-substituted-3-methyl-1-iodo-1-tributylstannylbutane, which is in turn dehydrohalogenated with DBU, yielding a 3-substituted-3-methyl-1-tributylstannyl-1-butene, for example, 3-(4-chlorophenyl)-3-methyl-1-tributylstannyl-1-butene. This intermediate is then reacted with 3,5-diamino-6-bromo-1,2,4-triazine in the presence of tri-2-furylphosphine and tris(dibenzylidineacetone)dipalladium(0), yielding the targeted 3,5-diamino-6-(3-substituted-3-methyl-1-butenyl)-1,2,4-triazine (V). The intermediate 3,5-diamino-6-bromo-1,2,4-triazine is prepared by bromination of the commercially available 3-amino-1,2,4-triazine with N-bromosuccinimide then, by the method of Rykowski [Synthesis (1985), 884–886], treatment of the bromo intermediate with liquid ammonia and potassium permanganate, yielding 3,5-diamino-6-bromo-1,2,4-triazine. Example 5 provides a detailed procedure to prepare this type of compound.

In Schema 4, where T is C≡C, X is C(CH$_3$)$_2$ and m and n are 1, an appropriately substituted benzylhalide reagent is treated with potassium cyanide, yielding the corresponding substituted acetonitrile, for example, 4-trifluoromethylacetonitrile. The acetonitrile is then treated with potassium tert.-butoxide and an alkyl iodide, for example, methyl iodide, yielding the 2-methyl-2-substituted-propanenitrile. This intermediate was subsequently treated with diisobutylaluminum hydride, then with bromomethyl triphenylphosphonium bromide, yielding the corresponding 1-bromo-3-methyl-3-substituted-1-butene, for example, 1-bromo-3-methyl-3-(4-trifluoromethylphenyl)-1-butene. The 1-butene intermediate is in turn dehydrohalogenated with potassium tert.-butoxide, then reacted with 3,5-diamino-6-bromo-1,2,4-triazine under mild basic conditions in the presence of copper iodide and bis(triphenylphosphine)palladium(II) chloride, yielding the targeted 3,5-diamino-6-(3-substituted-3-methyl-1-butynyl)-1,2,4-triazine, for example, 3,5-diamino-6-[3-(4-trifluorophenyl)-3-methyl-1-butynyl]-1,2,4-triazine. Example 6 provides a detailed procedure to prepare this type of compound.

The compounds thus prepared can be further derivatized to provide additional compounds within the scope of the present invention. For example, reacting any of the 3,5-diamino compounds disclosed herein with an acid anhydride will yield a substituted amino derivative. One such compound may be prepared by the reaction of, for example, 3,5-diamino-6-(3,4-dichlorophenyl)-1,2,4-triazine with one equivalent of acetic anhydride in refluxing dioxane, yielding the corresponding 5-amino-3-methylcarbonylamino-6-(3,4-dichlorophenyl)-1,2,4-triazine. Example 7 provides a detailed procedure to prepare this type of compound.

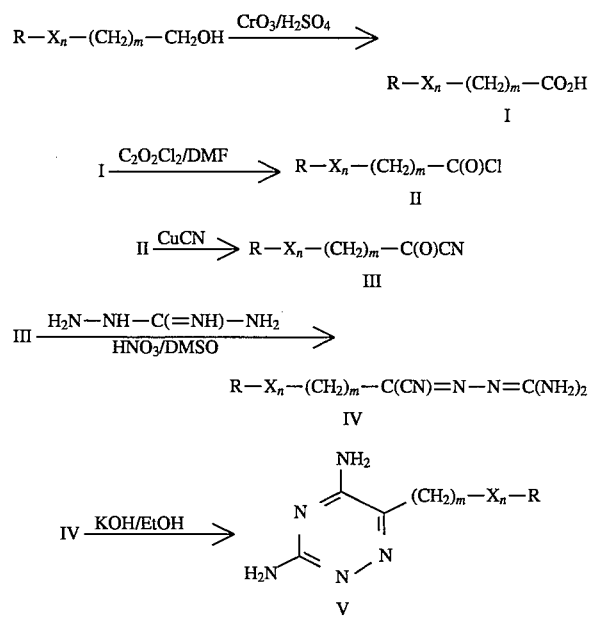

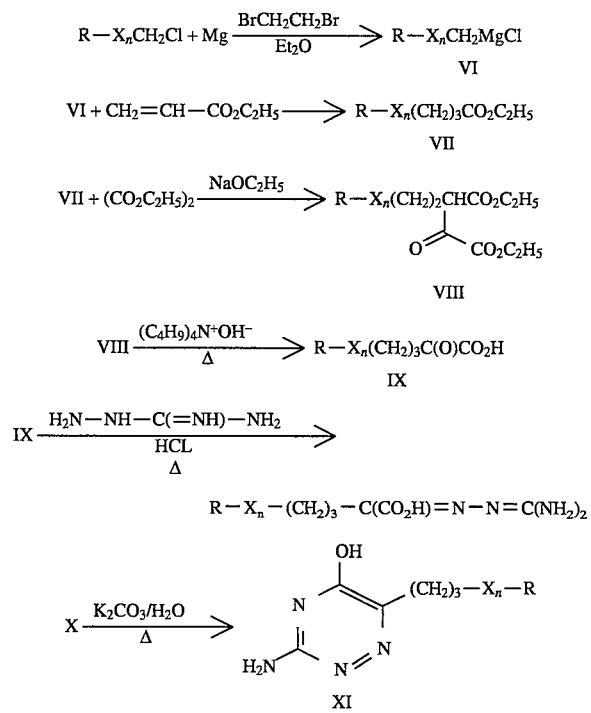

5

-continued
Schema 2

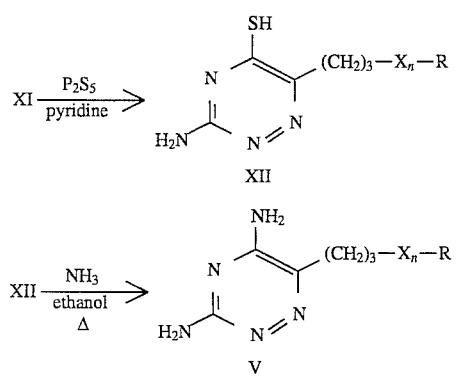

Schema 3

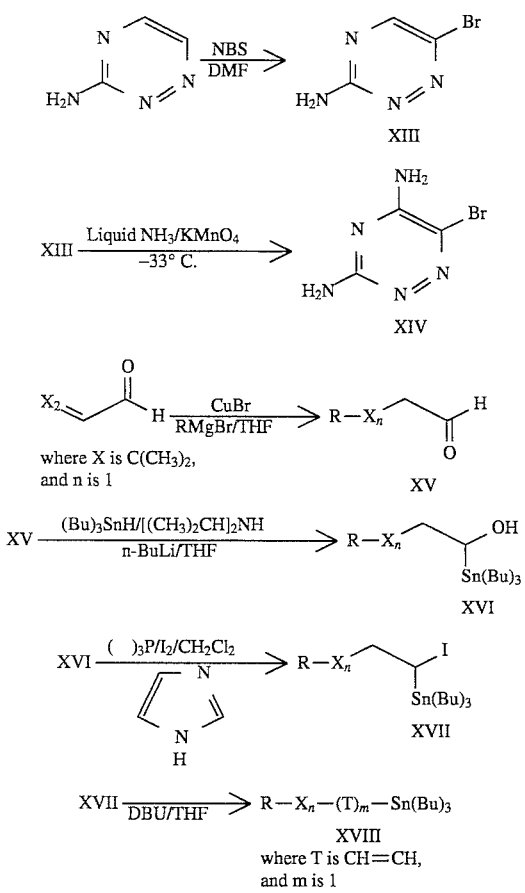

6

Schema 4

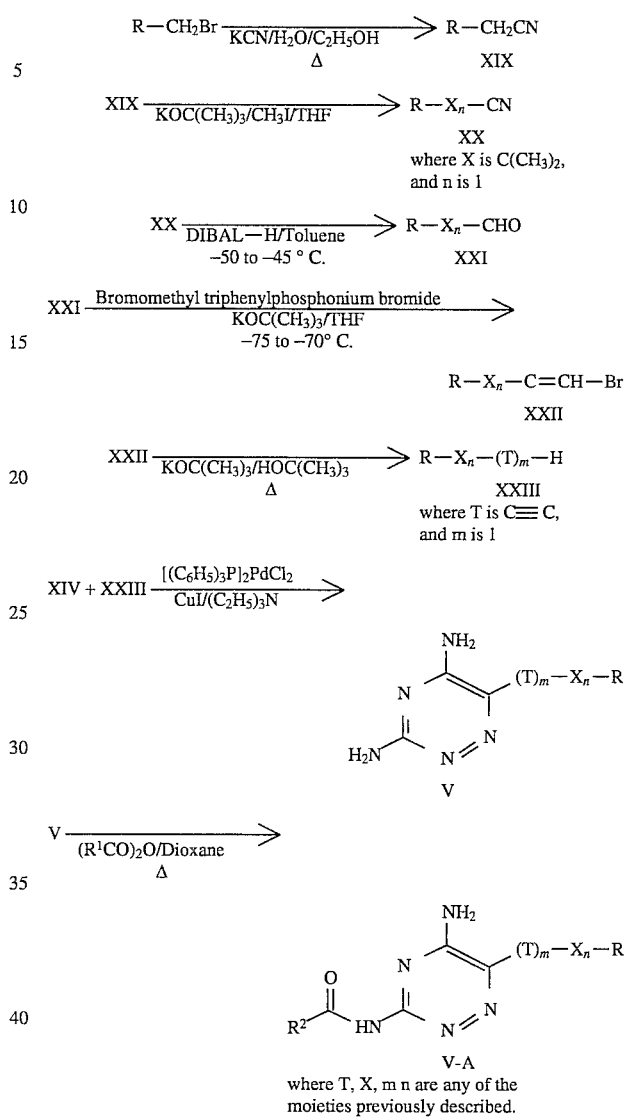

where T, X, m n are any of the moieties previously described.

EXAMPLES

The following examples are by way of illustration only, and are not intended to limit the scope of the invention claimed herein.

The products of these examples are summarized in Table 1 below, while their corresponding empirical formulas and characterizing data are listed in Table 2.

EXAMPLE 1

3,5-DIAMINO-6-(3,3-DIMETHYL-3-SILABUTYL)-1,2,4-TRIAZINE (Compound 8)

Step A Synthesis of 4,4-dimethyl-4-silapentanoic acid

To 12.5 mL of water was added 8.73 g (0.0873 mole) of chromium trioxide which was mixed until all solid had dissolved. This solution was immersed in an ice/water bath, and 13.4 g (7.3 mL, 0.137 mole) of concentrated sulfuric acid (18M) was added cautiously. This was followed by the addition of 25 mL of water. The solution was then cooled to 0°–5° C. and added to a stirred solution of 16.5 g (0.125 mole) of 4,4-dimethyl-4-silapentanol in 800 mL of acetone which had been cooled to 0°–10° C. in an ice/water bath. During the addition the temperature was maintained at 20° C., and stirring was continued for three hours after the addition was complete. At the conclusion of this period sodium bisulfite was added to the reaction mixture in small portions until the brown color of chromic acid had disappeared from the upper layer. The two layers were separated, and the dense, green lower layer was extracted with 200 mL of petroleum ether. The layers were separated, and the upper layer was added to the upper layer which had been previously separated. This caused two phases to form. The layers were separated, and the lower layer was added to the lower layer from the reaction mixture. The combined lower layers were extracted three times with 200 mL of petroleum ether. The extracts were combined with the previously separated petroleum ether extract, and this mixture was successively washed twice with a saturated aqueous solution of sodium chloride, twice with a saturated aqueous solution of sodium bicarbonate, and finally with a saturated aqueous solution of sodium chloride. After being dried over anhydrous magnesium sulfate, the solvent was evaporated from the combined extracts under reduced pressure, leaving 4,4-dimethyl-4-silapentanoic acid as a residue. The NMR spectrum was consistent with the proposed structure. This is the method described in *Organic Synthesis*, Vol. V, p 866.

Step B Synthesis of 4,4-dimethyl-4-silapentanoic acid chloride

In a flask were place 13.4 g (0.0918 mole) of 4,4-dimethyl-4-silapentanoic acid, 100 mL of diethyl ether, and two drops of N,N-dimethylformamide. To this solution, which was cooled in an ice/water bath, was added 13.98 g (0.110 mole) of oxalyl chloride in diethyl ether in a dropwise manner. Upon completion of addition, the temperature was allowed to rise to ambient conditions, and the mixture was stirred for approximately 16 hours. At the conclusion of this period the solvent was evaporated from the reaction mixture under reduced pressure, leaving 10.42 g of 4,4-dimethyl-4-silapentanoic acid chloride as a residue. The NMR spectrum was consistent with the proposed structure.

Step C Synthesis of 4,4-dimethyl-4-silapentanoyl cyanide

In a flask were placed 5.0 g (0.032 mole) of 4,4-dimethyl-4-silapentanoic acid chloride and 2.89 g (0.032 mole) of copper(I) cyanide. This mixture was heated at approximately 150°–200° C. for a period of 50 minutes after which it was cooled to ambient temperature. Methylene chloride was added to the reaction mixture which was then filtered. The solvent was evaporated from the filtrate under reduced pressure, leaving 1.5 g of 4,4-dimethyl-4-silapentanoyl cyanide as a residue.

Step D Synthesis of N-[(3,3-dimethyl-3-silabutyl)(cyano)methylidene]-N'-diaminomethylidenehydrazine In a flask were placed 1.34 g (0.0098 mole) of aminoguanidine bicarbonate and 25 mL of 8N nitric acid. This mixture was cooled with an ice/water bath, and 1.45 g (0.00935 mole) of 4,4-dimethyl-4-silapentanoyl cyanide in 5 mL of dimethyl sulfoxide was added dropwise to it. The resulting mixture was stirred at 0° C. for 30 minutes and then at ambient temperature for approximately 16 hours. During the reaction a white precipitate formed. This was filtered from the reaction mixture, yielding 2 g of crude N-[(3,3-dimethyl-3-silabutyl)(cyano)methylidene]-N'-diaminomethylidenehydrazine which was used in the next reaction without further purification.

Step E Synthesis of 3,5-diamino-6-(3,3-dimethyl-3-silabutyl)-1,2,4-triazine

In a flask were placed 10 g (0.18 mole) of potassium hydroxide and 100 mL of ethanol. After complete dissolution of the potassium hydroxide, 2 g (0.009 mole) of N-[(3,3-dimethyl-3-silabutyl)(cyano)methylidene]-N' -diaminomethylidenehydrazine was added to the reaction mixture which was then heated at reflux for one hour. At the conclusion of this period, 50 mL of water was added to the reaction mixture. The solvent was evaporated from the mixture, and the residue was filtered, yielding 0.8 g of 3,5-diamino-6-(3,3-dimethyl-3-silabutyl)-1,2,4-triazine, m.p. 203°–204° C. The NMR spectrum was consistent with the proposed structure.

EXAMPLE 2

3,5-DIAMINO-6-(4-METHYL-4-PHENYL-4-SILAPENTYL)-1,2,4-TRIAZINE (Compound 14)

Step A Synthesis of ethyl 5-methyl-5-phenyl-5-silahexanoate

To a stirred mixture of 7.9 g (0.329 mole) of magnesium metal and 0.5 mL of 1,2-dibromoethane in 150 mL of diethyl ether was added dropwise a solution of 50 g (0.271 mole) of (chloromethyl)dimethylphenylsilane in 100 mL of diethyl ether. The addition required 30 minutes. Upon completion of addition, the resultant solution was transferred using a cannula to a flask containing 15.5 g (0.108 mole) of copper(I) bromide which was under a nitrogen atmosphere and was cooled in a dry ice/acetone bath. To this flask was added dropwise a solution 10.8 g (0.108 mole) of ethyl acrylate in 50 mL of diethyl ether. The addition required 40 minutes. Upon completion of addition, the reaction mixture was allowed to warm to −10° C. It was then diluted with 400 mL of diethyl ether, and a solution of 14.2 g of ammonium chloride in 40 mL of water was added dropwise while maintaining the temperature at −10° C. to 0° C. Upon completion of addition, the reaction mixture was filtered, and the solvent was evaporated under reduced pressure, leaving a residue. This residue was passed through a column of silica gel, eluting with diethyl ether/petroleum ether (5:95). The product-containing fractions were combined, and the solvent was evaporated, yielding 12.95 g of ethyl 5-methyl-5-phenyl-5-silahexanoate as an oil.

Step B Synthesis of diethyl 2-oxo-3-(3-methyl-3-phenyl-3-silabutyl)succinate

In a flask under a nitrogen atmosphere were placed 1.7 g (0.075 mole) metallic sodium and 75 mL of absolute ethanol. When all of the sodium had reacted, the remaining ethanol was evaporated, leaving solid sodium ethoxide. To this solid were added successively 100 mL of dry tetrahydrofuran, 11.0 g (0.075 mole) of diethyl oxalate, and 12.95 g (0.0517 mole) of ethyl 5-methyl-5-phenyl-5-silahexanoate. This mixture was heated at reflux for one hour after which it was cooled to ambient temperature before being poured into 240 mL of 0.5N hydrochloric acid. This mixture was extracted with 200 mL of diethyl ether. The extract was evaporated under reduced pressure, leaving 16.7 g of diethyl 2-oxo-3-(3-methyl-3-phenyl-3-silabutyl)succinate as an oil. This reaction was repeated to provide additional product for subsequent steps in this synthesis.

Step C Synthesis of 6-methyl-6-phenyl-2-oxo-6-silaheptanoic acid

In a flask were placed 27.1 g (0.0773 mole) of diethyl 2-oxo-3-(3-methyl-3-phenyl-3-silabutyl)succinate, 301 g (0.464 mole) of 40 wt % tetrabutyl ammonium hydroxide, and 500 mL of water. This mixture was heated at reflux under a nitrogen atmosphere for 25 minutes after which it was cooled to ambient temperature. The reaction mixture was acidified with 50 mL of 12N hydrochloric acid and then extracted twice with 400 mL of diethyl ether. The extracts were combined and washed with 100 mL of 3N hydrochloric acid after which the solvent was evaporated under reduced pressure, yielding 17.45 g of 6-methyl-6-phenyl-2-oxo-6-silaheptanoic acid as an oil.

Step D Synthesis of N-[(4-methyl-4-phenyl-4-silapentyl)(carboxy)methylidene]-N'-diaminomethylidenehydrazine In a flask were placed 8.94 g (0.0657 mole) of aminoguanidine bicarbonate and 65.7 mL of 1N hydrochloric acid which were mixed slowly until complete dissolution resulted. To this solution was added 16.45 g (0.0657 mole) of 6-methyl-6-phenyl-2-oxo-6-silaheptanoic acid as an oil, and the resulting mixture was heated at reflux for 20 minutes. To this hot solution was added 250 mL of water, and the resulting mixture was allowed to cool to ambient temperature with stirring. A precipitate formed which was removed by filtration. The filter cake was stirred with 100 mL of methanol, and the solid was recovered by filtration. This solid was dried in vacuo, yielding 13.1 g of N-[(4-methyl-4-phenyl-4-silapentyl)(carboxy)methylidene] -N'-diaminomethylidenehydrazine.

Step E Synthesis of 3-amino-5-hydroxy-6-(4-methyl-4-phenyl-4 -silapentyl)-1,2,4-triazine In a flask were placed 8.00 g (0.0261 mole) of N-[(4-methyl-4-phenyl-4 -silapentyl)(carboxy)methylidene]-N'-diaminomethylidenehydrazine, 5.4 g (0.039 mole) of potassium carbonate, and 80 mL of water. This mixture was heated at reflux for three hours under a nitrogen atmosphere. While still hot, the mixture, which contained solids, was filtered. The filter cake was retained, and the filtrate was neutralized with 10 mL of acetic acid and allowed to cool to ambient temperature, causing a precipitate to form. This solid was also collected by filtration and then recrystallized from 60 mL of ethanol. An NMR spectrum of the recrystallized material indicated that it consisted of starting material and 3-amino-5-hydroxy-6-(4-methyl-4-phenyl-4-silapentyl)-1,2,4-triazine (1:1). The filtrate was evaporated under reduced pressure, leaving a residue which was mixed with the recrystallized solid and the solid which had been filtered from the reaction mixture initially. To this mixture was added 400 mL of water and 7.0 g (0.051 mole) of potassium carbonate. This mixture was heated at reflux under a nitrogen atmosphere for approximately 17 hours after which it was filtered. The filtrate was neutralized with 30 mL of acetic acid, and the resulting precipitate was collected by filtration. This solid was stirred with methanol and again collected by filtration, yielding, after being dried, 3.45 g of 3 -amino-5-hydroxy-6-(4-methyl-4-phenyl-4-silapentyl)-1, 2,4-triazine, m.p. 250°–252° C. The NMR and IR spectra were consistent with the proposed structure.

Step F Synthesis of 3-amino-5-mercapto-6-(4-methyl-4-phenyl-4 -silapentyl)-1,2,4-triazine In a flask were placed 2.90 g (0.0105 mole) of 3-amino-5-hydroxy-6-(4 -methyl-4-phenyl-4-silapentyl)-1,2,4-triazine, 8.94 g (0.0201 mole) of phosphorus pentasulfide, and 40 mL of pyridine. This mixture was heated at reflux under a nitrogen atmosphere for one hour. The reaction mixture was concentrated under reduced pressure to a volume of approximately 25 mL and then mixed with 150 mL of ice water. The resulting mixture was warmed on a steam bath for 4 hours after which it was cooled to ambient temperature. An orange solid was collected from this mixture by filtration and was stirred with 60 mL of methanol. Filtration of this mixture yielded 2.70 g of 3-amino-5-mercapto-6-(4-methyl-4-phenyl-4-silapentyl)-1,2,4 -triazine, m.p. 255°–257° C. (decomposition). The NMR and IR spectra were consistent with the proposed structure.

Step G Synthesis of 3,5-diamino-6-(4-methyl-4-phenyl-4-silapentyl)-1,2,4-triazine Ethanol (80 mL) was cooled to −70° C., and 10 g (0.59 mole) of ammonia was bubbled into the ethanol. To this solution in a pressure bottle was added 1.90 g (0.0062 mole) of 3-amino-5-mercapto-6-(4-methyl-4 -phenyl-4-silapentyl)-1,2,4-triazine. The bottle was sealed and placed in an oil bath heated to 140° C. for two hours. During this period some of the ammonia escaped from the pressure bottle. After cooling to ambient temperature, the pressure bottle was further cooled in a dry ice/acetone bath before being opened. The solvent was then evaporated under reduced pressure, leaving a residue which was then passed through a column of silica gel, eluting with N,N-dimethylformamide/ethyl acetate (1:9 and then 1:4). The product-containing fractions were combined, and the solvent was evaporated under reduced pressure, leaving a brown oil as the residue. This oil was extracted with 100 mL of hot diethyl ether. When the ether solution was cooled to 5° C., a red-brown solid precipitated. This solid was isolated by filtration and analyzed by NMR spectroscopy which showed that it was composed of 95% 3,5-diamino-6-(4-methyl-4-phenyl-4-silapentyl)-1,2,4-triazine and 5% starting material. The red-brown solid was passed through a column of silica gel, eluting with N,N-dimethylformamide/ethyl acetate (1:19 and 1:9), but this did not separate the two components. The product-containing fractions were combined, and the solvent evaporated under reduced pressure, leaving an oil as the residue. This oil was triturated with diethyl ether, yielding 0.60 g of 3,5-diamino-6-(4-methyl-4 -phenyl-4-silapentyl)-1,2,4-triazine as an off-white solid, m.p. 132°–133° C. The NMR and IR spectra were consistent with the proposed structure; however, the NMR revealed that it contained approximately 16.7% ethyl acetate. Elemental Analysis [Calculated for $C_{14}H_{21}N_5Si.0.10(C_4H_8O_2)$]:

|  | Calculated | Found* |
|---|---|---|
| carbon | 58.38 | 58.51 |
| hydrogen | 7.43 | 7.31 |
| nitrogen | 23.65 | 23.69 |

*Average of two analyses

EXAMPLE 3

3,5-DIAMINO-6-[3-(4-CHLOROPHENYL)BUTYL)-1,2,4-TRIAZINE (Compound 10)

Step A Synthesis of 2-(4-chlorophenyl)propanol

To a suspension of 3.8 g (0.10 mole) of lithium aluminum hydride in 50 mL of tetrahydrofuran is added dropwise a solution of 18.4 g (0.10 mole) of 2-(4-chlorophenyl)propionic acid in 200 mL of tetrahydrofuran. This reaction mixture is allowed to stir at ambient temperature for a period of approximately 16 hours after which it is cooled by an ice/water bath. To the cooled reaction mixture are added in sequence 4 mL of water, 4 mL of a 10% aqueous solution of sodium hydroxide, and 12 mL of water. The mixture is then filtered, and the filter cake is washed with diethyl ether. The diethyl ether wash is combined with the filtrate, and the combination is dried over anhydrous magnesium sulfate.

The solvents are then evaporated under reduced pressure, leaving 2-(4-chlorophenyl)propanol as a residue.

Step B Synthesis of 2-(4-chlorophenyl)propionaldehyde

To a solution of 19.8 g (0.092 mole) of pyridinium chlorochromate in 80 mL of methylene chloride is added a solution of 7.8 g (0.046 mole) of 2-(4-chlorophenyl)propanol in 20 mL of methylene chloride. After one hour this mixture is diluted with 100 mL of diethyl ether, and the remaining solution is decanted from the insoluble material. Additional diethyl ether is added to the solids, and, after being mixed thoroughly, the solution is decanted from the solids and combined with the original solution. The combination is washed sequentially with 10 mL of a 10% aqueous solution of sodium hydroxide, 10 mL of 10% hydrochloric acid, and finally with 10 mL of water. After being dried over an hydrous magnesium sulfate, this solution is evaporated under reduced pressure, leaving a residue. This residue is passed through a column of silica gel, eluting with ethyl acetate/hexane (5:95). Product-containing fractions are combined, and the solvent is evaporated from the combined fractions under reduced pressure, leaving 2-(4-chlorophenyl)propionaldehyde as the residue.

Step C Synthesis of ethyl 4-(4-chlorophenyl)-2-pentenoate

To a stirred solution of 3.9 g (0.023 mole) of 2-(4-chlorophenyl)propionaldehyde in 25 mL of 1,4-dioxane is added in one portion 9.0 g (0.026 mole) of (carbethoxymethylene)triphenylphosphorane. The reaction mixture is stirred for approximately 16 hours at ambient temperature after which the solvent is evaporated under reduced pressure, leaving a residue which is then dissolved in ethyl acetate. Approximately 10 g of silica gel is mixed with the resulting solution. The solvent is evaporated from this mixture, and the residue is placed in a sintered glass filter. The silica gel is then eluted with 100 mL of heptane/ethyl acetate (3:1). These solvents are evaporated under reduced pressure, leaving a residue. This residue is dissolved in 30 mL of heptane/ethyl acetate (9:1), treated with 5 g of silica gel, and filtered. The filtrate is evaporated under reduced pressure, leaving ethyl 4-(4-chlorophenyl)-2-pentenoate as a residue.

Step D Synthesis of ethyl 4-(4-chlorophenyl)pentanoate

A solution of 4.3 g (0.018 mole) of ethyl 4-(4-chlorophenyl)-2-pentenoate in 40 mL of ethanol is placed in a Parr hydrogen apparatus. To this solution is added approximately 0.1 g of platinum oxide. The bottle is capped and hydrogen gas is introduced into the reaction mixture until a stoichiometric amount of hydrogen has been absorbed. The reaction mixture is then filtered to remove the platinum oxide, and the solvent is evaporated from the filtrate under reduced pressure, leaving ethyl 4-(4-chlorophenyl)-2-pentanoate as a residue.

Step E Synthesis of 4-(4-chlorophenyl)pentanoic acid

In a flask are placed 3.85 g (0.016 mole) of ethyl 4-(4-chlorophenyl)-2-pentanoate in 25 mL of ethanol and 12.8 g (0.032 mole) of a 10% aqueous solution of sodium hydroxide. This mixture is stirred at ambient temperature for approximately 16 hours after which the ethanol is evaporated under reduced pressure, leaving a residue. To this residue is added 20 mL of water, and the resulting mixture is extracted once with 50 mL of diethyl ether. The aqueous layer is acidified with 10% aqueous hydrochloric acid, and this mixture is extracted three times with 50 mL of diethyl ether. The extracts are combined, washed with water, and dried over anhydrous magnesium sulfate. The solution is filtered, and the solvent is evaporated from the filtrate under reduced pressure, leaving 4-(4-chlorophenyl)pentanoic acid as the residue.

Step F Synthesis of 4-(4-chlorophenyl)pentanoic acid chloride

By the method of Example 1, Step B, 3.0 g (0.014 mole) of 4-(4-chlorophenyl)-2-pentanoic acid and 2.13 g (0.0168 mole) of oxalyl chloride are reacted in 50 mL of diethyl ether in the presence of 2 drops of N,N-dimethylformamide, producing 4-(4-chlorophenyl)pentanoic acid chloride.

Step G Synthesis of 4-(4-chlorophenyl)pentanoyl cyanide

By the method of Example 1, Step C, 2.44 g (0.011 mole) of 4-(4-chlorophenyl)-2-pentanoic acid chloride and 0.99 g (0.011 mole) of copper(I) cyanide are reacted, producing 4-(4-chlorophenyl)pentanoyl cyanide.

Step H Synthesis of N-[[3-(4-chlorophenyl)butyl](cyano)methylidene]-N'-diaminomethylidenehydrazine By the method of Example 1, Step D, 2.0 g (0.009 mole) of 4-(4-chlorophenyl)pentanoyl cyanide, 1.29 g (0.0095 mole) of aminoguanidine bicarbonate, 25 mL of 8N nitric acid, and 5 mL of dimethyl sulfoxide are reacted, yielding N-[[3-(4-chlorophenyl)butyl](cyano)methylidene]-N'-diaminomethylidenehydrazine as a precipitate.

Step I 3,5-Diamino-6-[3-(4-chlorophenyl)butyl]-1,2,4-triazine

By the method of Example 1, Step E, 2.2 g (0.008 mole) of N-[[3-(4-chlorophenyl)butyl](cyano)methylidene]-N'-diaminomethylidenehydrazine and 9.0 g (0.16 mole) of potassium hydroxide are reacted in 100 mL of ethanol, yielding 3,5-diamino-6-[3-(4-chlorophenyl)butyl]-1,2,4-triazine.

EXAMPLE 4

3,5-DIAMINO-6-[3-(2,4-DICHLOROPHENYL)PROPYL)-1,2,4-TRIAZINE
(Compound 13)

Step A Synthesis of 4-(2,4-dichlorophenyl)-3-butyn-1-ol

Under a nitrogen atmosphere 97.2 g (0.356 mole) of 2,4-dichloroiodobenzene, 3.21 g (0.0046 mole) of bis(triphenylphosphine)palladium(II) chloride, and 0.8 g (0.0042 mole) of copper(I) iodide were suspended in 50 mL of triethylamine and 100 mL of acetonitrile. This mixture was cooled in an ice/water bath to 0°–5° C., and 24.6 g (0.356 mole) of 3-butyn-1-ol dispersed in 25 mL of acetonitrile was added dropwise. Upon completion of addition, the reaction mixture was allowed to warm to ambient temperature at which it was stirred for approximately 16 hours. The solvent was evaporated from the reaction mixture under reduced pressure, leaving a brown oil as the residue. This oil was passed through a column of silica gel, eluting first with hexane and then with methylene chloride. Product-containing factions were combined, and the solvent was evaporated under reduced pressure, leaving 4-(2,4-dichlorophenyl)-3-butyn-1-ol as the residue. The NMR spectrum was consistent with the proposed structure.

Step B Synthesis of 4-(2,4-dichlorophenyl)-1-butanol

A mixture of 12.0 g (0.0558 mole) of 4-(2,4-dichlorophenyl)-3-butyn-1-ol and 0.4 g of platinum oxide in 280 mL of ethanol was placed in a Parr hydrogenator. Hydrogen gas was introduced into the reactor until there was no further uptake. Upon completion of the reaction, the reaction mixture was filtered to remove the platinum oxide catalyst, and then the solvent was evaporated under reduced pressure, leaving 4-(2,4-dichlorophenyl)-1-butanol as the residue. The NMR spectrum was consistent with proposed structure.

Step C Synthesis of 4-(2,4-dichlorophenyl)butanoic acid

By the method of Example 1, Step A, 3.63 g (0.0363 mole) of chromium trioxide, 5 mL of water, 5.6 g (0.056 mole) of 18M sulfuric acid, 10.4 mL of water, and 11.4 g (0.052 mole) of 4-(2,4-dichlorophenyl)-1-butanol in 332 mL of acetone are reacted, yielding 4-(2,4-dichlorophenyl)butanoic acid.

Step D Synthesis of 4-(2,4-dichlorophenyl)butanoic acid chloride

By the method of Example 1, Step B, 9.79 g (0.042 mole) of 4-(2,4-dichlorophenyl)butanoic acid and 5.8 g (0.050 mole) of oxalyl chloride are reacted in 75 mL of diethyl ether and two drops of N,N-dimethylformamide, yielding 4-(2,4-dichlorophenyl)butanoic acid chloride.

Step E Synthesis of 4-(2,4-dichlorophenyl)butanoyl cyanide

By the method of Example 1, Step C, 7.54 g (0.030 mole) of 4-(2,4-dichlorophenyl)butanoic acid chloride and 2.69 g (0.030 mole) of copper(I) cyanide are reacted, yielding 4-(2,4-dichlorophenyl)-butanoyl cyanide.

Step F Synthesis of N-[[3-(2,4-dichlorophenyl)propyl](cyano)methylidene]-N'-diaminomethylidenehydrazine By the method of Example 1, Step D, 2.42 g (0.010 mole) of 4-(2,4-dichlorophenyl)butanoyl cyanide, 1.50 g (0.011 mole) of aminoguanidine bicarbonate, 25 mL of 8N nitric acid, and 5 mL of dimethyl sulfoxide are reacted, yielding N-[[3-(2,4-dichlorophenyl)propyl](cyano)methylidene]-N'-diaminomethylidenehydrazine as a precipitate.

Step G 3,5-Diamino-6-[3-(2,4-dichlorophenyl)propyl]-1,2,4-triazine

By the method of Example 1, Step E, 2.4 g (0.008 mole) of N-[[3-(2,4-dichlorophenyl)propyl](cyano)methylidene]-N'-diaminomethylidenehydrazine and 9.0 g (0.16 mole) of potassium hydroxide are reacted in 100 mL of ethanol, yielding 3,5-diamino-6-[3-(2,4-dichlorophenyl)propyl]-1,2,4-triazine.

EXAMPLE 5

SYNTHESIS OF 3,5-DIAMINO-6-[3-(4-CHLORO-PHENYL)-3-METHYL-1-BUTENYL]-1,2,4-TRIAZINE (COMPOUND 40)

Step A Synthesis of 3-amino-6-bromo-1,2,4-triazine as an intermediate

A stirred solution of 6.1 grams (0.063 mole) of 3-amino-1,2,4-triazine in 125 mL of N,N-dimethylformamide is cooled in an ice bath, and a solution of 11.2 grams (0.063 mole) of N-bromosuccinimide in 125 mL of N,N-dimethylformamide is added dropwise during a 30 minute period, while maintaining the reaction mixture temperature at about 15°–25° C. Upon completion of addition, the reaction mixture is stirred at ambient temperature for about 20 hours. After this time, the reaction mixture is poured into 1 liter of aqueous 3N sodium hydroxide. The mixture is then diluted to a volume of about 1700 mL with distilled water. A solid precipitate is collected by filtration and dried under reduced pressure, yielding 3-amino-6-bromo-1,2,4-triazine.

Step B Synthesis of 3,5-diamino-6-bromo-1,2,4-triazine as an intermediate

A solution of 6.0 grams (0.038 mole) of potassium permanganate in about 300 mL of liquid ammonia (−33° C.) is stirred, and 5.3 grams (0.030 mole) of 3-amino-6-bromo-1,2,4-triazine is added portionwise. Upon completion of addition, the reaction mixture is maintained at −33° C. for 15 minutes. Ammonia is then evaporated and the residue is extracted with about 150 mL of hot 1-methylethanol. The solution is concentrated under reduced pressure, yielding 3,5-diamino-6-bromo-1,2,4-triazine.

Note: This compound may be prepared by the method of Rykowski; Synthesis (1985), 884–886.

Step C Synthesis of 3-(4-chlorophenyl)-3-methylbutyraldehyde as an intermediate

Under a nitrogen atmosphere, a stirred solution of 21.6 grams (0.10 mole) of 4-chlorophenylmagnesium bromide (1M in diethyl ether) in 100 mL of tetrahydrofuran was cooled to −15° C., and 0.7 gram (catalyst) of copper(I) bromide was added in one portion. Upon completion of addition, 9.7 mL (0.10 mole) of 3-methyl-2-butenal was added dropwise during a 1.5 hour period, while maintaining the reaction mixture temperature below −10° C. Upon completion of addition, the reaction mixture was allowed to warm to ambient temperature, where it stirred for about 18 hours. The reaction mixture was then poured into 300 mL of water and extracted with two 200 mL portions of diethyl ether. The combined extracts were dried with magnesium sulfate and filtered. The filtrate was concentrated under reduced pressure to a residue. The residue was subjected to column chromatography on silica gel, using 50% petroleum ether in methylene chloride. The appropriate product-containing fractions were combined and concentrated under reduced pressure, yielding 7.6 grams of 3-(4-chlorophenyl)-3-methylbutyraldehyde. The NMR spectrum was consistent with the proposed structure.

Step D Synthesis of 3-(4-chlorophenyl)-3-methyl-1-tributylstannylbutanol as an intermediate A stirred solution of 5.0 mL (0.036 mole) of diisopropylamine in 100 mL of tetrahydrofuran was cooled to 0° C., and 14.3 mL (0.036 mole) of n-butyllithium (2.5M in hexanes) was added dropwise. Upon completion of addition, 9.6 grams (0.036 mole) of tributyltin hydride was added dropwise during a 15 minute period. The reaction mixture was then stirred at 0° C. for 15 minutes. After this time the reaction mixture was cooled to −78° C., and a solution of 7.0 grams (0.036 mole) of 3-(4-chlorophenyl)-3-methylbutyraldehyde in 10 mL of tetrahydrofuran was added dropwise, while maintaining the reaction mixture temperature below −70° C. The complete addition required about 20 minutes. After this time the reaction mixture was stirred at below −70° C. for ten minutes. The reaction was then quenched by the dropwise addition of about 300 mL of aqueous dilute ammonium chloride solution to the cold reaction mixture. The complete addition required about 10 minutes. The cooling bath was removed, and the reaction mixture was extracted with two 200 mL portions of diethyl ether. The combined extracts were dried with magnesium sulfate and filtered. The filtrate was concentrated under reduced pressure, at a temperature of less than 30° C., yielding 17.4 grams of 3-(4-chlorophenyl)-3-methyl-1-tributylstannylbutanol.

Step E Synthesis of 3-(4-chlorophenyl)-3-methyl-1-iodo-1-tributylstannylbutane as an intermediate A solution of 14.0 grams (0.053 mole) of triphenylphosphine in about 54 mL of methylene chloride was stirred, and 3.6 grams (0.053 mole) of imidazole was added. Upon completion of addition, the reaction mixture was stirred about 45 minutes until the imidazole dissolved. The reaction mixture was then cooled in an ice bath, and 13.6 grams (0.053 mole) iodine was added portionwise. Upon completion of addition, the reaction mixture was allowed to warm to ambient temperature, where it stirred for about 15 minutes until the iodine dissolved. After this time the reaction mixture was cooled to 0° C., and a solution of 17.4 grams (0.036 mole) of 3-(4-chlorophenyl)-3-methyl-1-tributylstannylbutanol in about 36 mL of methylene chloride was added dropwise while maintaining the reaction mixture temperature below 5° C. Upon completion of addition, the reaction mixture was allowed to warm to ambient temperature where it stirred for about 18 hours. The reaction mixture was then taken up in about 100 mL of acetonitrile and extracted with three 150 mL portions of hexane. The combined extracts were concentrated under reduced pressure to a residue. The residue was subjected to column chromatography on silica gel, using petroleum ether as the eluant. The product-containing fractions were combined and concentrated under reduced pressure, yielding 8.7 grams of 3-(4-chlorophenyl)-3-methyl-1-iodo-1-tributylstannylbutane.

The NMR spectrum was consistent with the proposed structure.

Step F Synthesis of 3-(4-chlorophenyl)-3-methyl-1-tributylstannyl-1-butene as an intermediate Under a nitrogen atmosphere, a stirred solution of 8.7 grams (0.015 mole) of 3-(4-chlorophenyl)-3-methyl-1-iodo-1-tributylstannylbutane and 6.5 mL (0.045 mole) of 1,8-diazabicyclo[5.4.0]undec-7-ene (DBU)in 50 mL of tetrahydrofuran was heated at reflux for about 18 hours. The reaction mixture was cooled and poured into about 225 mL of water. The mixture was then made acidic with aqueous 2N hydrochloric acid and extracted with two 150 mL portions of diethyl ether. The combined extracts were dried with magnesium sulfate and filtered. The filtrate was concentrated under reduced pressure to a residue. The residue was subjected to column chromatography on silica gel, using 5% methylene chloride in petroleum ether as the eluant. The product-containing fractions were combined and concentrated under reduced pressure, yielding 5.3 grams of 3-(4-chlorophenyl)-3-methyl-1-tributylstannyl-1-butene. The NMR spectrum was consistent with the proposed structure. NOTE: The procedure to prepare 3-(4-chlorophenyl)-3-methyl-1-tributylstannyl-1-butene as shown in Steps C–F above is disclosed by J. M. Chong et al., JOC, (1993), 58, 523–527.

Step G Synthesis of 3,5-diamino-6-[3-(4-chlorophenyl)-3-methyl-1-butenyl]-1,2,4-triazine (Compound 40)

A mixture of 0.04 gram (catalyst) of tri-2-furylphosphine and 0.04 gram (catalyst) of tris(dibenzylidineacetone)dipalladium(0) in 30 mL of N,N-dimethylformamide is purged with dry nitrogen gas and stirred at ambient temperature for five minutes. After this time 0.9 gram (0.0048 mole) of 3,5-diamino-6-bromo-1,2,4-triazine (prepared in Step B of this Example) is added in one portion. The reaction vessel is then immersed in an oil bath that is preheated to 60° C. where it is maintained for about five minutes. After this time, 3.1 grams (0.0064 mole) of 1,1-difluoro-1-(4-chlorophenyl)-3-tributylstannyl-2-propene is added in one portion to the reaction mixture. The reaction mixture is again purged with dry nitrogen gas, and the oil bath temperature is brought to 80°–85° C. where it is maintained for about 18 hours. After this time the reaction mixture is diluted with 200 mL of water and extracted with two 200 mL portions of ethyl acetate. The combined extracts are then washed with three 100 mL portions of an aqueous solution of 5% lithium chloride. The organic layer is concentrated under reduced pressure to a residue. The residue is purified by column chromatography, yielding 3,5-diamino-6-[3-(4-chlorophenyl)-3-methyl-1-butenyl]-1,2,4-triazine.

EXAMPLE 6

SYNTHESIS OF 3,5-DIAMINO-6-[3-(4-TRIFLUOROPHENYL)-3-METHYL-1-BUTYNYL]-1,2,4-TRIAZINE (COMPOUND 53)

Step A Synthesis of 4-trifluoromethylphenylacetonitrile as an intermediate

A stirred solution of 250.0 grams (1.05 moles) of 4-trifluoromethylphenylmethyl bromide in 1000 mL of ethanol was heated to about 80° C., and a solution of 109.0 grams (1.67 moles) of potassium cyanide in about 275 mL of water was added. Upon completion of addition, the reaction mixture was stirred at 80° C. for about 1.75 hours. After this time the reaction mixture was cooled to ambient temperature and extracted with three portions of diethyl ether. The combined extracts were washed with two portions of water and one portion of an aqueous solution saturated with sodium chloride. The organic layer was dried with magnesium sulfate and filtered. The filtrate was concentrated under reduced pressure, yielding about 197 grams of 4-trifluoromethylphenylacetonitrile.

Step B Synthesis of 2-methyl-2-(4-trifluoromethylphenyl)propanenitrile as an intermediate A stirred solution of 101.3 grams (0.55 mole) of 4-trifluoromethylphenylacetonitrile in 300 mL of tetrahydrofuran was cooled in an ice-bath, and a solution of 194.1 grams (1.37 moles) of iodomethane in 100 mL of tetrahydrofuran was added. Upon completion of addition, a solution of 153.5 grams (1.37 moles) of potassium tert.-butoxide in 900 mL of tetrahydrofuran was then added dropwise. Upon completion of addition, the reaction mixture was stirred at ambient temperature for about 18 hours. The reaction mixture was stirred with about 400 mL of water, then aqueous 1N hydrochloric acid was added until the color of the reaction mixture changed from red to yellow. Water was then added to the reaction mixture to cause an oily residue to separate from the mixture. The water was decanted from the oil, and the oil was dissolved in diethyl ether. The ether solution was washed with two portions of water and two portions of an aqueous solution saturated with sodium chloride. The ether solution was then dried with magnesium sulfate and filtered. The filtrate was concentrated under reduced pressure, yielding about 119.8 grams of 2-methyl-2-(4-trifluoromethylphenyl)propanenitrile. The NMR spectrum was consistent with the proposed structure.

Step C Synthesis of 2-methyl-2-(4-trifluoromethylphenyl)propanaldehyde as an intermediate A stirred solution of 119.8 grams (0.56 mole) of 2-methyl-2-(4-trifluoromethylphenyl)propanenitrile in 100 mL of toluene was cooled to −50° C., and 487 mL (0.73 mole) of diisobutylaluminium hydride (1.5M in toluene) was added dropwise during a 45 minute period while keeping the reaction mixture temperature between −45° and −50° C. Upon completion of addition, the reaction mixture was stirred at −50° C. for 30 minutes. The reaction mixture was then warmed to about 0° C., where it stirred for an additional 30 minutes. After this time, the reaction mixture was carefully poured into 1000 mL of ice-cold aqueous 1.5M sulfuric acid. The resultant mixture was stirred for about three hours, then it was allowed to stand for about 18 hours. The aqueous layer was separated and extracted with 200 mL of diethyl ether. The organic layer and the diethyl ether extract were combined and dried with magnesium sulfate. The mixture was filtered, and the filtrate was concentrated under reduced pressure, yielding 102.3 grams of 2-methyl-2-(4-trifluoromethylphenyl)propanaldehyde. The NMR spectrum was consistent with the proposed structure.

Step D Synthesis of bromomethyl triphenylphosphonium bromide as an intermediate

Under a nitrogen atmosphere, a stirred solution of 215.0 grams (0.82 mole) of triphenylphosphine and 115 mL (1.64 moles) of dibromomethane in 600 mL of toluene was heated at reflux for about eight hours. After this time a solid was collected by filtration. The filtrate was again heated to reflux where it stirred for an additional eight hours. The mixture was cooled and additional solid was collected by filtration. The two solids were combined, yielding about 280 grams of bromomethyl triphenylphosphonium bromide.

Step E Synthesis of cis/trans-1-bromo-3-methyl-3-(4-trifluoromethylphenyl)-1-butene as an intermediate Under a nitrogen atmosphere, a stirred solution of 101.0 grams (0.23 mole) of bromomethyl triphenylphosphonium bromide in 400 mL of tetrahydrofuran was cooled in a dry ice-acetone bath, and 26.0 grams (0.23 mole) of potassium tert.-butoxide was added portionwise while maintaining the reaction mixture temperature between −70° and −75° C. Upon completion of addition, the reaction mixture was stirred at −75° C. for about 90 minutes. After this time a solution of 50.0 grams (0.23 mole) of 2-methyl-2-(4-trifluoromethylphenyl)propanaldehyde (prepared in Step C of this Example) in 100 mL of tetrahydrofuran was added dropwise while maintaining the reaction mixture temperature below −65° C. Upon completion of addition, the reaction mixture was allowed to warm to ambient temperature as it stirred for about 18 hours. The reaction mixture was then poured into 500 mL of water and extracted with two 300 mL portions of diethyl ether. The combined extracts were dried with magnesium sulfate and filtered. The filtrate was concentrated under reduced pressure to a residual oil. The oil was subjected to column chromatography on silica gel using petroleum ether as the eluant. The product-containing fractions were combined and concentrated under reduced pressure, yielding 40.9 grams of cis/trans-1-bromo-3-methyl-3-(4-trifluoromethylphenyl)-1-butene. The NMR spectrum was consistent with the proposed structure.

Step F Synthesis of 3-methyl-3-(4-trifluoromethylphenyl)-1-butyne as an intermediate Under a nitrogen atmosphere, a stirred solution of 40.9 grams (0.14 mole) of cis/trans-1-bromo-3-methyl-3-(4-trifluoromethylphenyl)-1-butene and 47.0 grams (0.42 mole) of potassium tert.-butoxide in 300 mL of tert.-butanol was heated at reflux for about three hours. After this time the reaction mixture was allowed to cool to ambient temperature as it stirred for about 18 hours. The reaction mixture was then poured into 300 mL of water and extracted with one 200 mL portion of diethyl ether. The extract was dried with magnesium sulfate, filtered, and concentrated under reduced pressure to a residue. The residue was subjected to column chromatography on silica gel using petroleum ether as the eluant. The product-containing fractions were combined and concentrated under reduced pressure, yielding 25.2 grams of 3-methyl-3-(4-trifluoromethylphenyl)-1-butyne. The NMR spectrum was consistent with the proposed structure.

Step G Synthesis of 3,5-diamino-6-[3-(4-trifluorophenyl)-3-methyl-1-butynyl]-1,2,4-triazine (Compound 53)

A reaction vessel containing 0.6 gram (0.0032 mole) of 3,5-diamino-6-bromo-1,2,4-triazine, 0.9 gram (0.0042 mole) of 3-methyl-3-(4-trifluoromethylphenyl)-1-butyne, 0.2 gram (catalyst) of bis(triphenylphosphine)palladium(II) chloride, 0.05 gram (catalyst) of copper iodide, and 8 mL of triethylamine is evacuated and refilled with dry nitrogen gas three times. The reaction mixture is then stirred at ambient temperature for about 60 hours. After this time, the reaction mixture is diluted with 100 mL of water. The mixture is then extracted with three 75 mL portions of ethyl acetate. The combined extracts are washed with three 75 mL portions of an aqueous 5% lithium chloride solution. The organic layer is dried with sodium sulfate and filtered. The filtrate is concentrated under reduced pressure, and the residue is subjected to column chromatography. The appropriate product-containing fractions are combined and concentrated under reduced pressure, yielding 3,5-diamino-6-[3-(4-trifluorophenyl)-3-methyl-1-butynyl]-1,2,4-triazine.

EXAMPLE 7

SYNTHESIS OF 5-AMINO-3-METHYLCARBONYLAMINO-6-(3,4-DICHLOROPHENYL)-1,2,4-TRIAZINE (COMPOUND 59)

A stirring mixture of 5.0 grams (0.020 mole) of 3,5-diamino-6-(3,4-dichlorophenyl)-1,2,4-triazine (Compound 24; disclosed in J. Med. Chem., 1972, Vol. 15, No 8. 859–861), 2.0 grams (0.020 mole) of acetic anhydride and 0.01 gram (catalyst) of 4-dimethylaminopyridine in 40 mL of dioxane is heated at reflux for about two hours. The mixture is cooled and concentrated under reduced pressure to a residue. The residue is purified by column chromatography on silica gel, yielding 5-amino-3-methylcarbonylamino-6-(3,4-dichlorophenyl)-1,2,4-triazine.

TABLE 1

6-Substituted-3,5-diamino-1,2,4-triazines

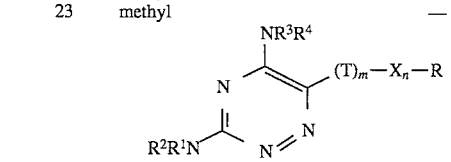

| Compound | R | X | m | n |
|---|---|---|---|---|
| 1 | phenyl | — | 0 | 0 |
| 2 | 1-naphthyl | — | 0 | 0 |
| 3 | 1,1'-biphenyl-3-yl | — | 0 | 0 |
| 4 | 4'-fluoro-1,1'-biphenyl-3-yl | — | 0 | 0 |
| 5 | vinyl | — | 2 | 0 |
| 6 | 4-ethylphenyl | — | 2 | 0 |
| 7 | 5-bromo-2,4-dichlorophenyl | — | 2 | 0 |
| 8 | methyl | —Si(CH$_3$)$_2$— | 2 | 1 |
| 9 | 4-chlorophenyl | —Si(CH$_3$)$_2$— | 2 | 1 |
| 10 | 4-chlorophenyl | —CH(CH$_3$)— | 2 | 1 |
| 11 | 4-chlorophenyl | —C(CH$_3$)$_2$— | 2 | 1 |
| 12 | 4-chlorophenyl | — | 3 | 0 |
| 13 | 2,4-dichlorophenyl | — | 3 | 0 |
| 14 | phenyl | —Si(CH$_3$)$_2$— | 3 | 1 |
| 15 | 4-chlorophenyl | —Si(CH$_3$)$_2$— | 3 | 1 |
| 16 | 4-chlorophenyl | —CH(CH$_3$)— | 3 | 1 |
| 17 | 4-chlorophenyl | —C(CH$_3$)$_2$— | 3 | 1 |
| 18 | 4-chlorophenyl | — | 4 | 0 |
| 19 | 2,4-dichlorophenyl | — | 4 | 0 |
| 20 | cyclopentyl | O | 4 | 1 |
| 21 | 4-propylsulfonylphenyl* | O | 4 | 1 |
| 22 | methyl | — | 6 | 0 |
| 23 | methyl | — | 12 | 0 | where R$^1$, R$^2$, R$^3$, and R$^4$ are hydrogen.

| 24 | 3,4-dichlorophenyl | — | 0 | 0 | where T is CH$_2$, and R$^1$, R$^2$, R$^3$, and R$^4$ are hydrogen.

| 25 | 4-chlorophenyl | — | 3 | 0 |
| 26 | 2,4-dichlorophenyl | — | 3 | 0 |
| 27 | 3,5-dichlorophenyl | — | 3 | 0 |
| 28 | 4-trifluoromethylphenyl | — | 3 | 0 |
| 29 | 3,5-di(trifluoromethyl)phenyl | — | 3 | 0 |
| 30 | 4-chlorophenyl | CH(CH$_3$) | 2 | 1 |

TABLE 1-continued

6-Substituted-3,5-diamino-1,2,4-triazines

| | | | | | |
|---|---|---|---|---|---|
| 31 | 2,4-dichlorophenyl | CH(CH$_3$) | 2 | 1 | |
| 32 | 3,5-dichlorophenyl | CH(CH$_3$) | 2 | 1 | |
| 33 | 4-trifluoromethylphenyl | CH(CH$_3$) | 2 | 1 | |
| 34 | 3,5-di(trifluoromethyl)-phenyl | CH(CH$_3$) | 2 | 1 | |
| 35 | 4-chlorophenyl | C(CH$_3$)$_2$ | 2 | 1 | |
| 36 | 2,4-dichlorophenyl | C(CH$_3$)$_2$ | 2 | 1 | |
| 37 | 3,5-dichlorophenyl | C(CH$_3$)$_2$ | 2 | 1 | |
| 38 | 4-trifluoromethylphenyl | C(CH$_3$)$_2$ | 2 | 1 | |
| 39 | 3,5-di(trifluoromethyl)-phenyl | C(CH$_3$)$_2$ | 2 | 1 | | where T is CH=CH, and R$^1$, R$^2$, R$^3$, and R$^4$ are hydrogen.

| | | | | |
|---|---|---|---|---|
| 40 | 4-chlorophenyl | CH(CH$_3$) | 1 | 1 |
| 41 | 2,4-dichlorophenyl | CH(CH$_3$) | 1 | 1 |
| 42 | 3,5-dichlorophenyl | CH(CH$_3$) | 1 | 1 |
| 43 | 4-trifluoromethylphenyl | CH(CH$_3$) | 1 | 1 |
| 44 | 3,5-di(trifluoromethyl)-phenyl | CH(CH$_3$) | 1 | 1 |
| 45 | 4-chlorophenyl | C(CH$_3$)$_2$ | 1 | 1 |
| 46 | 2,4-dichlorophenyl | C(CH$_3$)$_2$ | 1 | 1 |
| 47 | 3,5-dichlorophenyl | C(CH$_3$)$_2$ | 1 | 1 |
| 48 | 4-trifluoromethylphenyl | C(CH$_3$)$_2$ | 1 | 1 |
| 49 | 3,5-di(trifluoromethyl)-phenyl | C(CH$_3$)$_2$ | 1 | 1 | where T is C≡C, and R$^1$, R$^2$, R$^3$, and R$^4$ are hydrogen.

| | | | | |
|---|---|---|---|---|
| 50 | 4-chlorophenyl | C(CH$_3$)$_2$ | 1 | 1 |
| 51 | 2,4-dichlorophenyl | C(CH$_3$)$_2$ | 1 | 1 |
| 52 | 3,5-dichlorophenyl | C(CH$_3$)$_2$ | 1 | 1 |
| 53 | 4-trifluoromethylphenyl | C(CH$_3$)$_2$ | 1 | 1 |
| 54 | 3,5-di(trifluoromethyl)phenyl | C(CH$_3$)$_2$ | 1 | 1 | where R$^2$ and R$^4$ are hydrogen; m and n are 0; and R is 3,4-dichlorophenyl.

| Compound | R$^1$ | R$^3$ |
|---|---|---|
| 55 | —CH$_3$ | H |
| 56 | H | —CH$_3$ |
| 57 | —C$_2$H$_5$ | —C$_2$H$_5$ |
| 58 | —CH$_3$ | —C(=O)R$^5$, R$^5$ is —CH$_3$ |
| 59 | —C(=O)R$^5$, R$^5$ is —CH$_3$ | —CH$_3$ |

*Isolated as the N,N-dimethylformamide complex

TABLE 2

Characterizing Properties

| Compound No | Melting Point/ Physical State | Empirical Formula |
|---|---|---|
| 1 | 216–218° C. | C$_9$H$_9$N$_5$ |
| 2 | SOLID | C$_{13}$H$_{11}$N$_5$ |
| 5 | 120–125° C. | C$_7$H$_{11}$N$_5$ |
| 6 | 201–203° C. | C$_{13}$H$_{17}$N$_5$ |
| 7 | 261–263° C. | C$_{11}$H$_{10}$BrCl$_2$N$_5$ |
| 8 | 203–204° C. | C$_8$H$_{17}$N$_5$Si |
| 14 | 132–133° C. | C$_{14}$H$_{21}$N$_5$Si |
| 20 | 147–148.5° C. | C$_{12}$H$_{21}$N$_5$O |
| 21 | 124–126° C. | C$_{16}$H$_{23}$N$_5$O$_3$S.C$_3$H$_7$NO |
| 22 | 175–176° C. | C$_{10}$H$_{19}$N$_5$ |
| 23 | 170.0–172.0° C. | C$_{16}$H$_{31}$N$_5$ |

Insecticide Formulations

In the normal use of the insecticidal substituted triazines of the present invention, they usually will not be employed free from admixture or dilution, but ordinarily will be used in a suitable formulated composition compatible with the method of application and comprising an insecticidally effective amount of the triazine. The triazines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present substituted triazines may be applied, for example, as sprays, dusts, or granules to the area where pest control is desired, the type of application varying of course with the pest and the environment. Thus, the triazines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these triazine compounds.

Granules may comprise porous or nonporous particles, such as attapulgite clay or sand, for example, which serve as carriers for the triazines. The granule particles are relatively large, a diameter of about 400–2500 microns typically. The particles are either impregnated with the triazine from solution or coated with the triazine, adhesive sometimes being employed. Granules generally contain 0.05–10%, preferably 0.5–5%, active ingredient as the insecticidally effective amount.

Dusts are admixtures of the triazines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which acts carriers for the insecticide. These finely divided solids have an average particle size of less than about 50 microns. A typical dust formulation useful for controlling insects contains 1 part of Compound 8 and 99 parts of talc.

The triazines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% triazine, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

By way of illustration, compound 8 is formulated as a 10% wettable powder (10% WP) as follows:

| COMPONENT | AMOUNT (wt/wt) |
|---|---|
| Compound 8 | 10.1% |
| Wetting Agent | 5.0% |
| Dispersing Agent | 3.8% |
| Wetting/Dispersing Agent | 0.9% |
| Diluent | 80.2% |

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the triazines with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl taurides; alkylaryl polyether alcohols; sulfates of higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention were tested in the laboratory as dimethyl sulfoxide solutions incorporated into an artificial insect diet or as aqueous acetone or methanol solutions containing a small amount of octylphenoxypolyethoxyethanol surfactant for use as foliar sprays. An insecticidally effective amount of substituted triazine in an insecticidal composition diluted for application is normally in the range of about 0.001% to about 8% by weight. Many variations of spraying and dusting compositions known in the art may be used by substituting the triazine of this invention into compositions known or apparent in the art.

The insecticidal compositions of this invention may be formulated with other active ingredients, including other insecticides, nematicides, acaricides, fungicides, plant growth regulators, fertilizers, etc.

In using the compositions to control insects, it is only necessary that an insecticidally effective amount of triazine be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

Biological Data

Candidate insecticides were incorporated into an artificial diet for evaluation of insecticidal activity against the tobacco budworm (*Heliothis virescens* [Fabricius]).

Stock solutions of test chemical in dimethyl sulfoxide were prepared for each rate of application. The rates of application, expressed as the negative log of the molar concentration, and the corresponding concentrations of the stock solution prepared for each rate are shown below:

| Stock Solution | Rate of Application |
|---|---|
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65–70° C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethyl sulfoxide at the levels used in the test chemical-treated diet was poured into the five wells in the third row of the tray. Each tray therefore contained one test chemical at a single rate of application, together with an untreated control. Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. These results are reported in Table 3, below.

Candidate insecticides with high $PI_{50}$ values from the diet test were tested for insecticidal activity in foliar evaluations against tobacco budworm, beet armyworm (*Spodoptera exigua* [Hubner]), and cabbage looper (*Trichoplusia ni* [Hubner]).

In these tests against tobacco budworm and beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxy-ethanol in distilled water. Four replicates, each containing one chick pea plant, for each rate of application of test chemical were sprayed. The treated plants were transferred to a hood where they were kept until the spray had dried.

The four chick pea plants for each replicate treated with test chemical as described above were removed from their pots by cutting the stems just above the soil line. The excised leaves and stems from the four plants in each replicate were placed in individual 8-ounce paper cups, which contained a moistened filter paper. Five second-instar (6 days old) tobacco budworms or beet armyworms (7–8 days old) were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead, moribund, and live insects were counted. Using the insect counts, the efficacy of the test chemical was expressed in percent control. Percent control is derived from the total number of dead insects (TD) plus the total number of moribund insects (TM) as compared to the total number of insects (TI) in the tests:

$$\% \text{ Control} = \frac{TD + TM}{TI} \times 100$$

The condition of the test plants was also observed for phytotoxicity and for reduction of feeding damage as compared to an untreated control. The results of these tests are shown in Table 4, below.

Foliar tests with cabbage looper were conducted in the same manner as described above, the difference being that pinto bean plants (*Phaseolus vulgaris*) were used.

TABLE 3

Insecticidal Activity of 6-Substituted-3,5-diamino-1,2,4-triazines Incorporated into the Diet of Tobacco Budworm

| Compound No. | Rate (−log M) | Percent Inhibition | PI$_{50}$ | Percent Mortality |
|---|---|---|---|---|
| 1 | 8 | ND | NM | 0 |
|   | 7 | ND |    | 0 |
|   | 6 | ND |    | 0 |
|   | 5 | −15 |   | 0 |
|   | 4 | 13 |    | 0 |
| 2 | 4 | 16 | NM | 0 |
| 5 | 5 | 7 | NM | 0 |
|   | 4 | 13 |    | 0 |
| 6 | 5 | −20 | NM | 0 |
|   | 4 | 20 |    | 0 |
| 7 | 5 | −7 | NM | 0 |
|   | 4 | 3 |    | 15 |
| 8 | 6 | 1 | 4.9 | 0 |
|   | 5 | 52 |    | 5 |
|   | 4 | 80 |    | 5 |
| 14 | 6 | −1 | 4.6 | 0 |
|    | 5 | 24 |    | 0 |
|    | 4 | 81 |    | 5 |
| 20 | 4 | 1 | NM | 0 |
| 21 | 5 | −14 | <4.0 | 0 |
|    | 4 | 22 |     | 0 |
| 22 | 5 | 3 | <4.0 | 0 |
|    | 4 | 27 |     | 0 |
| 23 | 5 | 16 | <4.0 | 0 |
|    | 4 | 27 |     | 0 |

FOOTNOTES
1 The rate of application is expressed as the negative log of the molar concentration of the test compound in the diet.
2 Percent growth inhibition is derived from the total weight of the insects (IW) at each rate of application in the test relative to the total weight of insects in an untreated control,
% Gr. Inh. = [IW (control) − IW (test)/IW (control)] × 100
3 A minus % growth inhibition indicates that the insects weighed more at the termination of the test than those in the untreated control.
4 pI$_{50}$ is the negative log of the concentration of the test chemical that provides 50% growth inhibition in the test insects.
5 Percent mortality is derived from the number of dead insects (TD) relative to the total number of insects (TI) used in the test, $$\% \text{ Moratality} = \frac{TD}{TI} \times 100$$

TABLE 4

Insecticidal Activity of 6-Substituted-3,5-diamino-1,2,4-triazines Applied as Foliar Sprays

| Compound No. | Rate of Application (ppm) | Percent Control[1] | | |
|---|---|---|---|---|
| | | TBW | CL | BAW |
| 8 | 3000 | 90 | 95 | 95 |
|   | 1000 | 70 | 60 | 40 |
|   | 300 | 15 | 20 | 5 |
|   | 100 | 0 | 20 | 0 |
|   | 30 | 0 | 20 | 0 |
| 14 | 3000 | 0 | 30 | 5 |
|    | 1000 | 0 | 31 | 0 |
|    | 300 | 5 | 21 | 5 |
|    | 100 | 0 | 15 | 0 |
|    | 30 | 5 | 5 | 0 |
| 22 | 1000 |   | 0 | 0 |
|    | 300 | 5 | 10 | 0 |
|    | 100 | 0 | 5 | 0 |
|    | 30 | 0 | 5 | 0 |
|    | 10 | 0 | 10 | 0 |
|    | 3 | 0 |   |   |

FOOTNOTES
[1]TBW — tobacco budworm
CL — cabbage looper
BAW — beet armyworm

We claim:
1. An insecticidal composition comprising, in admixture with an agriculturally acceptable carrier, an insecticidally effective amount of a 1,2,4-triazine compound of the formula

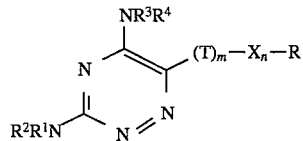

wherein
m is 1 to 12; n is 0 or 1; T is CH$_2$, CH=CH, or C≡C; X is Si(CH$_3$)$_2$, C(CH$_3$)$_2$, CH(CH$_3$), or O; and R is methyl, vinyl, cyclopentyl, phenyl, naphthyl, or a substituted phenyl of the formula:

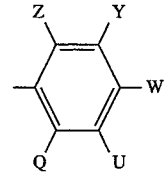

wherein
Q is hydrogen or chloro; U is hydrogen, chloro, trifluoromethyl, phenyl, or 4-fluorophenyl; W is hydrogen, ethyl, chloro, trifluoromethyl, or propylsulfonyl; Y is hydrogen, chloro, bromo or trifluoromethyl; and Z is hydrogen;
R$^1$, R$^2$, R$^3$, and R$^4$ are independently selected from the group consisting of hydrogen, —CH$_3$, —C$_2$H$_5$, or —C(=O)R$^5$, where R$^5$ is straight or branched chain lower alkyl of one to three carbon atoms, —CH$_2$OCH$_2$CH$_3$, —CH$_2$OCH$_2$CH$_2$CH$_3$, —CH$_2$CH$_2$OCH$_3$, or —CH$_2$CH$_2$OCH$_2$CH$_3$;
with the proviso that when T is alkylene or acetylene, m must be 1;
and agriculturally acceptable salts thereof.

2. The composition of claim 1 wherein R is methyl or phenyl.

3. The composition of claim 1 wherein X is —Si(CH$_3$)$_2$—.

4. The composition of claim 1 wherein R is methyl; X is —Si(CH$_3$)$_2$—; m is 2; and n is 1.

5. The composition of claim 1 wherein R is phenyl; X is —Si(CH$_3$)$_2$—; m is 3; and n is 1.

6. A method for controlling insects which comprises applying to the locus where control is desired an insecticidal amount of the composition of claim 1.

7. A method for controlling insects which comprises applying to the locus where control is desired an insecticidal amount of the composition of claim 2.

8. A method for controlling insects which comprises applying to the locus where control is desired an insecticidal amount of the composition of claim 3.

9. A method for controlling insects which comprises applying to the locus where control is desired an insecticidal amount of the composition of claim 4.

10. A method for controlling insects which comprises applying to the locus where control is desired an insecticidal amount of the composition of claim 5.

11. A compound having the formula

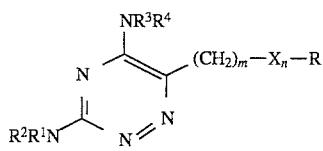

wherein m is 1 to 12; n is 0 or 1; X is Si(CH$_3$)$_2$, C(CH$_3$)$_2$, CH(CH$_3$), or O; and R is methyl, vinyl, cyclopentyl, phenyl, naphthyl, or a substituted phenyl of the formula:

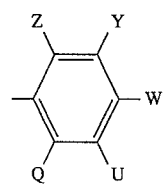

wherein

Q is hydrogen or chloro; U is hydrogen, chloro, trifluoromethyl, phenyl, or 4-fluorophenyl; W is hydrogen, ethyl, chloro, trifluoromethyl, or propylsulfonyl; Y is hydrogen, chloro, bromo or trifluoromethyl; and Z is hydrogen;

R$^1$, R$^2$, R$^3$, and R$^4$ are independently selected from the group consisting of hydrogen, —CH$_3$, —C$_2$H$_5$, or —C(=O)R$^5$, where R$^5$ is straight or branched chain lower alkyl of one to three carbon atoms, —CH$_2$OCH$_2$CH$_3$, —CH$_2$OCH$_2$CH$_2$CH$_3$, —CH$_2$CH$_2$OCH$_3$, or —CH$_2$CH$_2$OCH$_2$CH$_3$;

and agriculturally acceptable salts thereof.

12. The compound of claim 11 wherein R is methyl or phenyl.

13. The compound of claim 11 wherein X is —Si(CH$_3$)$_2$—.

14. The compound of claim 11 wherein R is methyl; X is —Si(CH$_3$)$_2$—; m is 2; and n is 1.

15. The compound of claim 11 wherein R is phenyl; X is —Si(CH$_3$)$_2$—; m is 3; and n is 1.

* * * * *